US009909998B2

(12) United States Patent
Patterson et al.

(10) Patent No.: US 9,909,998 B2
(45) Date of Patent: Mar. 6, 2018

(54) BUFFER GAS COOLING AND MIXTURE ANALYSIS (71) Applicant: PRESIDENT AND FELLOWS OF HARVARD COLLEGE, Cambridge, MA (US)

(72) Inventors: David S. Patterson, Somerville, MA (US); John M. Doyle, Belmont, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 383 days.

(21) Appl. No.: 14/391,379

(22) PCT Filed: Mar. 13, 2013

(86) PCT No.: PCT/US2013/031041
§ 371 (c)(1),
(2) Date: Oct. 8, 2014

(87) PCT Pub. No.: WO2013/154732
PCT Pub. Date: Oct. 17, 2013

(65) Prior Publication Data
US 2015/0077137 A1  Mar. 19, 2015

Related U.S. Application Data (60) Provisional application No. 61/622,648, filed on Apr. 11, 2012.

(51) Int. Cl.
G01J 5/02 (2006.01)
G01N 22/00 (2006.01)
(Continued)

(52) U.S. Cl.
CPC ......... *G01N 22/00* (2013.01); *G01N 33/0016* (2013.01); *G01N 21/3504* (2013.01); *G01N 21/6402* (2013.01)

(58) Field of Classification Search
CPC ............... G01N 22/00; G01N 33/0016; G01N 21/3504; G01N 21/6402
(Continued)

(56) References Cited

U.S. PATENT DOCUMENTS 4,827,134 A * 5/1989 Willner .................. G01N 30/80
250/341.6
5,245,405 A 9/1993 Mitchell et al.
(Continued)

FOREIGN PATENT DOCUMENTS

WO  WO-2011/130215 A1  10/2011

OTHER PUBLICATIONS

Egerov, D., et al., "Buffer-gas cooling of atomic and molecular beams," Physical Review A 66, pp. 043401-1 to 043401-8, (2002).
(Continued)

Primary Examiner — Farhana Hoque
(74) Attorney, Agent, or Firm — Foley & Lardner LLP; Cliff Z. Liu (57) ABSTRACT An apparatus for spectroscopy of a gas mixture is described. Such an apparatus includes a gas mixing system configured to mix a hot analyte gas that includes at least one analyte species in a gas phase into a cold buffer gas, thereby forming a supersaturated mixture to be provided for spectroscopic analysis.

20 Claims, 8 Drawing Sheets (51) Int. Cl.
  *G01N 33/00* (2006.01)
  *G01N 21/3504* (2014.01)
  *G01N 21/64* (2006.01)
(58) Field of Classification Search
  USPC .............................. 324/637; 250/341.6, 352
  See application file for complete search history.

(56) References Cited

U.S. PATENT DOCUMENTS

2008/0191132 A1  8/2008  Boyle et al.
2008/0288182 A1  11/2008  Cline et al.

OTHER PUBLICATIONS

Egorov, D., et al., "Buffer-gas cooling of NH via the beam loaded buffer-gas method," Eur. Phys, J. D. 31, pp. 307-311, (2004). (Campbell).

Hatakeyama, A., et al. "Atomic Alkali-metal Gas Cells at Liquid-Helium Temperatures: Loading by Light-induced Atom Desorption," Physical Review A, 65, pp. 022904-1 to 022904-9, (2002).
International Search Report and Written Opinion for PCT/US2011/032042 dated Aug. 18, 2011.
International Search Report and Written Opinion received for PCT/US2013/031041 dated Jun. 28, 2013.
Patterson, D., and Doyle, J.M., "Cooling molecules in a cell for FTMW spectroscopy," Molecular Physics, vol. 110, Nos. 15-16, pp. 1757-1766, (2012).
Patterson, D., and Doyle, J.M., "Cooling molecules in a cell for FTMW spectroscopy," Molecular Physics, vol. 110, Nos. 15-16, pp. 1757-1766, (2012). Abstract Only.
Patterson, D., et al., "Intense atomic and molecular beams via neon buffer-gas cooling," New Journal of Physics, vol. 11, 14 pages, (2009).
International Preliminary Report on Patentability issued on PCT/US2013/031041, dated Oct. 23, 2014.

* cited by examiner

BUFFER GAS COOLING AND MIXTURE ANALYSIS

CROSS REFERENCE TO RELATED APPLICATION

This application is a National Stage Entry of PCT/US2013/031041 filed on Mar. 13, 2013, which claims the benefit of U.S. Provisional Application No. 61/622,648 filed on Apr. 11, 2012, the disclosure of which is incorporated herein by reference in its entirety.

STATEMENT REGARDING FEDERALLY SPONSORED RESEARCH OR DEVELOPMENT

This invention was made with Government support under Grant No. C10D10472, awarded by the National Science Foundation, and Grant No. DE-FG02-02ER15316, awarded by the Department of Energy. The Government has certain rights in this invention.

FIELD OF THE INVENTION

This disclosure generally relates to analysis of constituents of a gas mixture and, more particularly, spectroscopic analysis of such mixtures.

BACKGROUND

In many cases, it is desirable to identify what chemical species are in a gas mixture. One way to achieve this is through spectroscopy. In spectroscopy, each chemical species can interact with incident radiation in both linear and nonlinear ways to produce a spectrum that depends on the structure of that species. The spectrum can be an absorption spectrum or an emission spectrum. In either case, it often includes narrow features, namely absorption or emission spectral lines at particular well-defined frequencies. In a mixture including two or more non-interacting species, the spectrum of the mixture is a superposition of the spectra of the individual species. Thus, by inspecting the spectral lines of a mixture, one can in principle identify its constituent species.

A difficulty that arises in practical systems is that spectral lines can have finite width. This can result from limits in instrument resolution or, in some cases, from fundamental properties associated with chemical species. Thus, in a mixture with many constituents, the separation between spectral lines of different species or of different states or conformers of the same species can be less than the line width. As a result, individual spectral lines may not be resolvable. This undermines the ability to identify the individual species within the mixture. In practice, this difficulty in resolving spectral lines impedes room temperature spectroscopy from being an effective tool for chemical analysis of complex mixtures of molecules including more than about eight atoms.

Cooling a molecular gas can greatly reduce the number of states a molecule occupies, which in turn simplifies its spectrum. More specifically, cold molecules can occupy far fewer rotational and vibrational states than warm molecules. Cold molecular gases therefore can have much simpler spectra including far fewer and, in some cases, narrower lines than corresponding spectra for warm molecular gases. As a result, spectroscopy can be used to identify larger molecules when a mixture of the molecules is cold rather than when the mixture is warm. For the foregoing reasons, it is desirable to deliver cold gas phase molecules to a spectrometer.

It is against this background that a need arose to develop the embodiments described herein.

SUMMARY

In many cases, such as in microwave spectroscopy, widths of spectral lines can be set by collisions between analyte molecules and other molecules or buffer gas atoms. Lower buffer gas densities therefore can translate into narrower spectral lines. Advantageously, embodiments of this disclosure can achieve efficient cooling while maintaining such lower buffer gas densities, which can be, for example, at least about 10 times, at least about 100 times, or at least about 1,000 times lower than other buffer gas cooling approaches.

In one aspect, embodiments of this disclosure feature an apparatus for spectroscopy of a gas mixture. Such an apparatus includes a gas mixing system configured to mix a hot analyte gas that includes at least one analyte species in a gas phase into a cold buffer gas, thereby forming a supersaturated mixture to be provided for spectroscopic analysis.

In some embodiments, the gas mixing system includes an analyte gas transport system and a buffer gas transport system. The analyte gas transport system is configured to propel a hot analyte gas at a first temperature toward a volume in which the analyte gas is to be mixed with the buffer gas. The buffer gas transport system is configured to propel a buffer gas at a second temperature toward the volume, where the second temperature is lower than the first temperature.

Among the foregoing embodiments are those that also include a cold cell to receive the supersaturated mixture. The cold cell includes an interior chamber defined by walls maintained at a temperature selected to further cool the supersaturated mixture. In some of these embodiments, the cold cell includes a first aperture to fluidly connect the interior chamber to a first space external to the cold cell. Among these embodiments are those that also include an injection tube disposed to direct the analyte gas across a gap and toward the first aperture.

Some embodiments include a second aperture in the cold cell in addition to the first aperture. This second aperture fluidly connects the interior chamber to a second space external to the cold cell. The second aperture is configured to allow the cold mixture of the buffer gas and the analyte gas to enter this second space, where spectroscopy can be performed in a substantially collision free environment.

Embodiments of this disclosure can vary in terms of where mixing occurs. In some of the foregoing embodiments, a volume in which the analyte gas is to be mixed with the buffer gas includes at least a portion of the first space external to the cold cell. In others, this volume includes at least a portion of the interior chamber of the cold cell. In yet others, this volume includes at least a portion of the interior chamber of the cold cell and at least a portion of the first space external to the cold cell.

A variety of options are contemplated for the buffer gas transport system. For example, among these options are those in which the buffer gas transport system is configured to direct the buffer gas into the first space external to the cold cell, those in which it is configured to direct the buffer gas into the interior chamber, and those that include an annular manifold disposed in a region peripheral to the first aperture, where the manifold is formed with openings for providing fluid communication between an interior of the manifold and at least the first space external to the cold cell, and the buffer gas transport system is configured to direct the buffer gas into and through the annular manifold.

A variety of options also are contemplated for the analyte transport system. For example, among these options are those in which the analyte gas transport system includes an injection tube configured to direct the analyte gas in a direction toward the cold cell. In such embodiments, a spacing or other configuration of the injection tube is adjusted to maintain a thermal disconnect between the warm injection tube and the cold cell. In others, the analyte gas transport system includes an injection tube configured to direct the analyte gas directly into the interior chamber.

Some embodiments of the apparatus also include a spectroscopy module configured to expose the supersaturated mixture to electromagnetic radiation and to detect at least one of absorption and emission of electromagnetic radiation. Various types of spectroscopy modules can be used. For example, among the embodiments are those in which the spectroscopy module is configured to perform Fourier transform microwave (FTMW) spectroscopy, those in which the spectroscopy module is configured to perform microwave-microwave double-resonance spectroscopy, those in which the spectroscopy module is configured to perform infrared absorption spectroscopy, those in which the spectroscopy module is configured to perform infrared-microwave double-resonance spectroscopy, those in which the spectroscopy module is configured to perform infrared free induction decay spectroscopy, those in which the spectroscopy module is configured to perform optical free induction decay spectroscopy, those in which the spectroscopy module is configured to perform laser induced fluorescence spectroscopy, those in which the spectroscopy module is configured to perform infrared-ultraviolet double-resonance spectroscopy, those in which the spectroscopy module is configured to perform microwave-ultraviolet double-resonance spectroscopy, and those in which the spectroscopy module is configured to perform ultraviolet resonantly enhanced multi-photon ionization spectroscopy.

Some embodiments also include a microwave horn disposed to be in electromagnetic communication with the mixture, or a different form of a microwave antenna in electromagnetic communication with the mixture, where the antenna is connected by a microwave transmission line to at least one of a source and a recorder. Either of the above options can also include a microwave cavity to enhance at least one of absorption and emission of microwave radiation.

In another aspect, embodiments of this disclosure feature an apparatus for spectroscopy. Such an apparatus includes a cold cell including a refrigerated internal chamber, means for forming a supersaturated mixture of a hot analyte gas including at least one analyte species in a gas phase and a cold buffer gas, and means for introducing the supersaturated mixture into the internal chamber.

In some embodiments, the means for forming the supersaturated mixture includes means for mixing the hot analyte gas and the cold buffer gas in a space external to the cold cell. Among these embodiments are those in which the cold cell includes means for providing fluid communication between the internal chamber and the space external to the cold cell. In some embodiments, the means for forming the supersaturated mixture includes means for mixing the hot analyte gas and the cold buffer gas in the internal chamber of the cold cell.

In another aspect, embodiments of this disclosure feature a method for spectroscopic analysis of an analyte gas. Such a method includes mixing the analyte gas at a first temperature with a buffer gas at a second temperature lower than the first temperature, thereby forming a supersaturated mixture, and directing the mixture to enter a cold cell to be further cooled by the cold cell.

In some embodiments, the method also includes irradiating analyte molecules with electromagnetic radiation and recording data indicative of at least one of electromagnetic radiation emitted by the molecules and electromagnetic radiation absorbed by the molecules. Among these embodiments are those that further include analyzing the recorded data to identify at least one chemical species in the analyte gas.

In another aspect, embodiments of this disclosure feature an apparatus for spectroscopy of a gas mixture. Such an apparatus includes a cold cell and a gas transport system configured to combine an analyte gas at a first temperature with a buffer gas at a second temperature, resulting in a mixture at a third temperature that is lower than the first temperature, and to provide the mixture to the cold cell. Such an apparatus also includes a spectroscopy module to characterize the mixture.

Other aspects and embodiments of this disclosure are also contemplated. The foregoing summary and the following detailed description are not meant to restrict the disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

FIG. 4: (a) Schematic of a circuitry for FTMW spectroscopy. A brief (typically 100 ns) powerful (typically 0.3 Watt) microwave pulse is produced by a switchable solid-state amplifier (AML L1218-32) and directed into a cell via a 15 dB gain (4 cm×6 cm) microwave horn. This pulse gives a molecular gas a macroscopic oscillating dipole moment; radiation from this oscillating dipole is collected by a second 15 dB horn, amplified, downconverted to about 10 MHz, and digitized. A fast RF switch (Narda S123D) protects the low noise amplifier from damage from the polarization pulse. Under typical conditions, a lifetime of the free induction decay signal is set by helium-molecule inelastic collisions. Frequency values are typical values for detecting the 15,074.1 MHz transition in acetone. (b) A typical timing diagram, showing the polarization pulse gate, the detection gate, and the averaged free induction decay signal from cold benzonitrile.

DETAILED DESCRIPTION

Some embodiments of this disclosure feature an apparatus for spectroscopy of cold mixtures of gases. The apparatus includes a cold cell configured to produce and, in some cases, to contain a cold mixture of a buffer gas and an analyte gas, and a spectroscopy module that exposes the cold mixture to electromagnetic radiation and detects at least one of absorption and emission of electromagnetic radiation. This cold mixture is supersaturated, namely a partial pressure of the analyte gas in the mixture is higher and, in some cases, substantially higher than a vapor pressure of the analyte gas at the temperature of the cold mixture.

Figure 1:
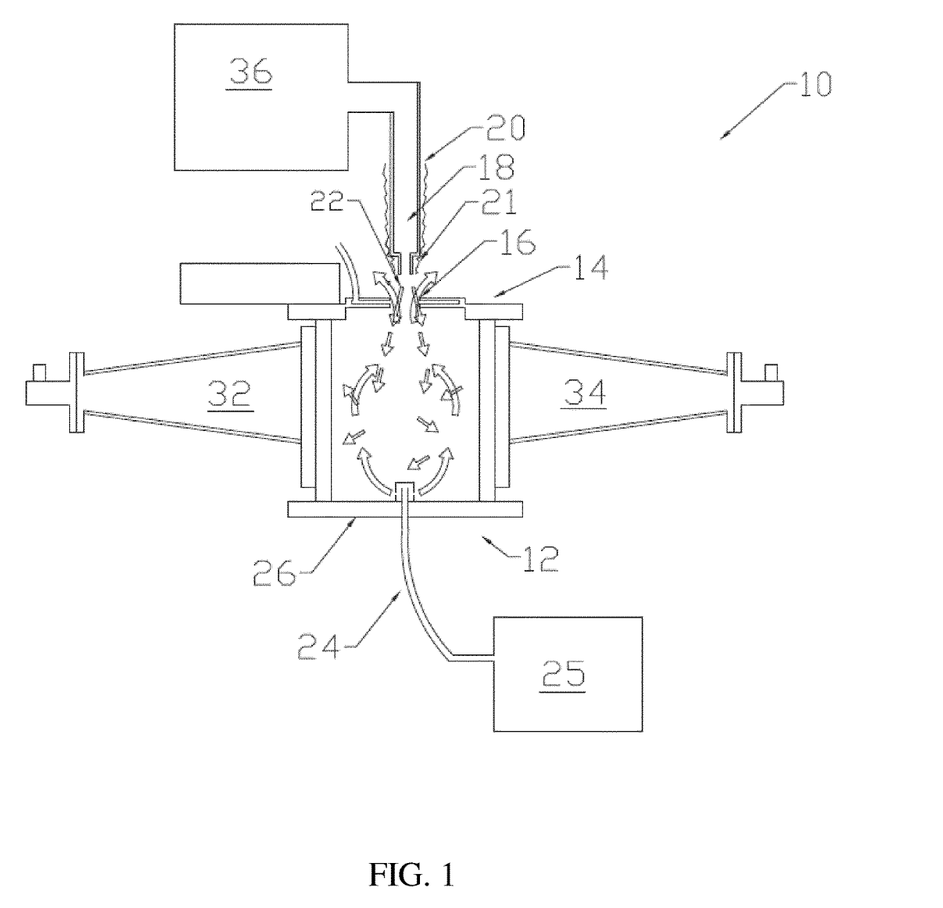
FIG. 1: Schematic of an apparatus including a cold cell and gas transport systems for cold molecule spectroscopy.
Figure 2:
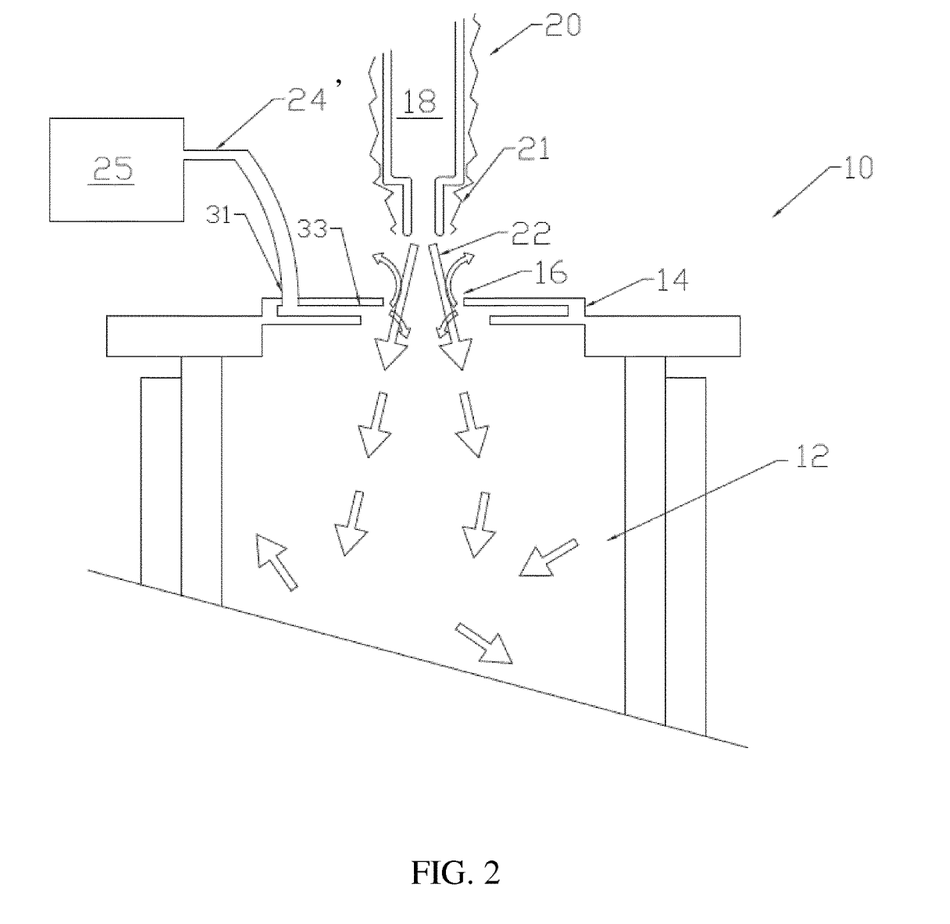
FIG. 2: Enlarged view of a portion of FIG. 1, showing a transport system of a buffer gas through an annular manifold.

Referring to FIGS. 1 and 2, an apparatus 10 for cold molecule spectroscopy includes a cold cell 12 including a wall 14 that forms an aperture 16. The aperture 16 can be substantially circular or can take on another shape such as elliptical, triangular, square, rectangular, or another polygonal or non-polygonal shape, and a diameter or other extent of the aperture 16 can be in the range of about 1 mm to about 5 cm, such as from about 2 mm to about 4 cm, from about 3 mm to about 3 cm, from about 4 mm to about 3 cm, from about 5 mm to about 2 cm, or from about 1 cm to about 2 cm. Separated from the aperture 16 is an injection tube 18 surrounded by an insulating jacket 20, with an opening 21 of the injection tube 18 being directed towards the aperture 16, but separated from the aperture 16 by a gap 22. The gap 22 can be in the range of about 1 mm to about 5 cm, such as from about 2 mm to about 4 cm, from about 3 mm to about 3 cm, from about 4 mm to about 3 cm, from about 5 mm to about 2 cm, or from about 1 cm to about 2 cm.

The apparatus 10 also includes a fill line 24 connected to a buffer gas source 25. In the illustrated embodiment, a buffer gas provided by the buffer gas source 25 is helium. However, the buffer gas can be another highly volatile gas, such as hydrogen gas ($H_2$), nitrogen gas ($N_2$), neon, argon, or can be a mixture of highly volatile gases. At least part of the apparatus 10 can be maintained under vacuum, with a space outside the cold cell 12 maintained at or below about $10^{-6}$ Torr by a vacuum pump, such as a cryopump.

In a first mode of operation of the apparatus 10 as shown in FIG. 1, the fill line 24 feeds the buffer gas through a wall 26 of the cold cell 12. The wall 26 can be a rear wall or a side wall of the cold cell 12. The buffer gas eventually exits the cold cell 12 through the aperture 16 and enters the gap 22 between the cold cell 12 and the injection tube 18.

In a second mode of operation of the apparatus 10 as shown in FIG. 2, another fill line 24' feeds the buffer gas into an annular manifold 31 surrounding a periphery of the aperture 16. The buffer gas is introduced from openings 33 in the annular manifold 31 and into the gap 22. A fraction of the buffer gas also enters the cold cell 12. This second mode of operation can mitigate against a net drift of the buffer gas, or a buffer gas "wind," within the cold cell 12 from the wall 26 to the wall 14. As a result, this mode of operation can mitigate against the likelihood that cold analyte molecules are hydrodynamically swept out of the cold cell 12 and back into the gap 22, thus representing a loss of molecules available for spectroscopic detection. A flow rate of the buffer gas as introduced through either the fill line 24 or the fill line 24' can be in the range of about 0.1 standard cm$^3$ min$^{-1}$ ("sccm") to about 20 sccm, such as from about 0.5 sccm to about 15 sccm, from about 1 sccm to about 10 sccm, or from about 2 sccm to about 8 sccm. Although the fill line 24 and the fill line 24' are shown connected to the same buffer gas source 25, it is contemplated that separate buffer gas sources can be included in other embodiments. Also, it is contemplated that the apparatus 10 can operate in another mode in which the buffer gas is introduced through both the fill line 24 and the fill line 24' substantially simultaneously. The buffer gas as introduced through either the fill line 24 or the fill line 24' can be maintained at a low temperature, such as up to about 12 K, up to about 10 K, up to about 8 K, up to about 6 K, up to about 5 K, up to about 4 K, or up to about 3 K, and down to about 1 K, down to about 0.5 K, or another lower threshold that can mitigate against condensation of the buffer gas out of the gas phase.

FIGS. 1 and 2 represent an in-cell embodiment in which spectroscopic analysis is performed on analyte molecules within the cold cell 12. Once the analyte molecules are in the cold cell 12, the molecules are characterized by a spectroscopy module. In the embodiment shown in FIGS. 1 and 2, the spectroscopy module is a FTMW spectrometer, including microwave horns 32 and 34 and associated circuitry. Specifically, the cold analyte molecules are polarized by a brief, strong microwave pulse (e.g., about 100 ns, about 300 mW) through the horn 32, and a resulting free induction decay is collected by the horn 34, amplified, mixed down to about 10 MHz or other suitable frequency, and digitized. Such an in-cell embodiment affords higher sensitivity, such as by allowing detection of analyte molecules with low concentrations of about 100 parts per million ("ppm") or under, about 10 ppm or under, about 1 ppm or under, about 100 parts per billion ("ppb") or under, about 10 ppb or under, or about 1 ppb or under.

Figure 3:
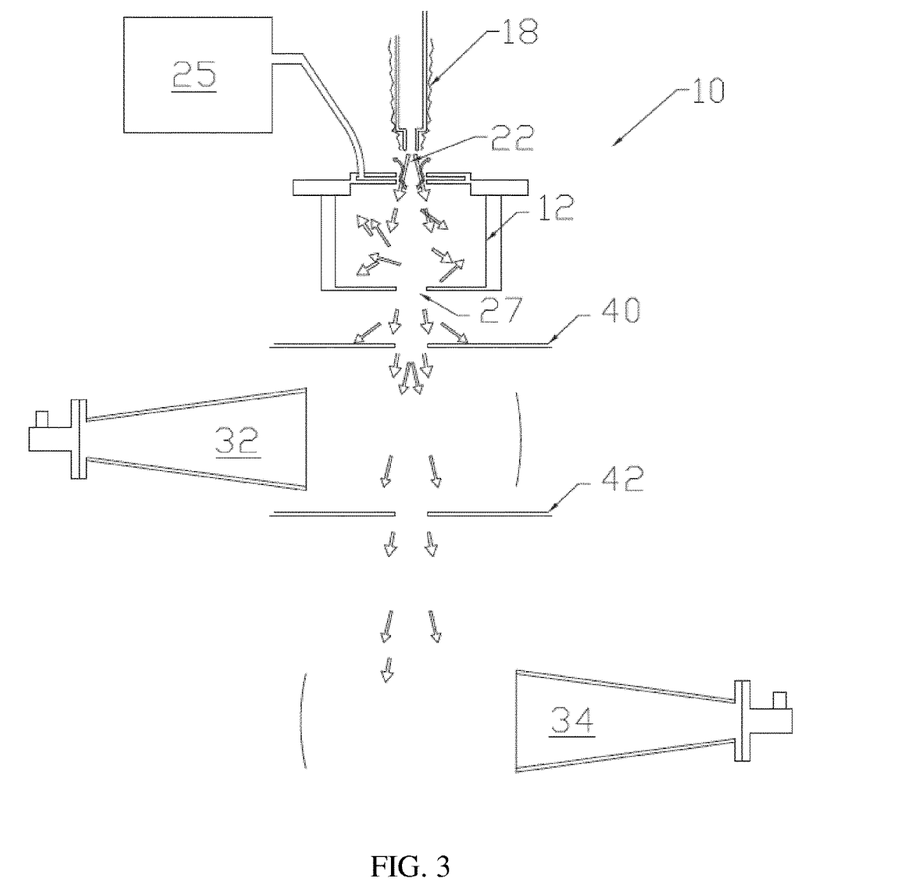
FIG. 3: Schematic of an apparatus for performing high resolution spectroscopy on a cold, slow beam of molecules.

In a further embodiment shown in FIG. 3, the cold cell 12 is similar to that shown in FIGS. 1 and 2 but with the addition of another aperture 27 formed in the wall 26. In this embodiment, cold analyte molecules pass through the aperture 27, and, shortly thereafter, the molecules enter a space (as defined by walls or panels 40 and 42) in which the molecules are characterized by a spectroscopy module, such as using antennas or optical devices. In the embodiment shown in FIG. 3, the microwave horns 32 and 34 are provided for use in spectroscopic analysis. In comparing with FIGS. 1 and 2 in which spectroscopic analysis takes place while analyte molecules are undergoing collisions, the out-of-cell embodiment shown in FIG. 3 allows spectroscopic analysis on analyte molecules that are not undergoing significant collisions. In some cases, the absence or near absence of collisions in the out-of-cell embodiment of FIG. 3 results in substantially narrower spectral lines and higher resolution. For example, spectral line widths for the in-cell embodiment can be set by gas collisions and can be in the range of about 5 kHz to about 70 kHz, such as from about 10 kHz to about 60 kHz or from about 20 kHz to about 50 kHz, while spectral line widths for the out-of-cell embodiment can be set by time-of-flight through the apparatus 10 and can be in the range of about 100 Hz to about 5 kHz, such as from about 200 Hz to about 4 kHz or from about 500 Hz to about 3 kHz.

Referring to FIGS. 1, 2, and 3, the injection tube 18 is connected to an analyte source 36 including the analyte gas, which can be a gaseous mixture of species referred as an analyte mixture, and which is delivered through the injection tube 18. The injection tube 18 can be heated to a temperature above room temperature to maintain less volatile analyte species in the gas phase as they traverse the injection tube 18, such as to a temperature of at least about 294 K, at least about 296 K, at least about 298 K, or at least about 300 K, and up to about 310 K, up to about 400 K, or more.

In some embodiments, the analyte source 36 includes a vaporizer to convert condensed phase analyte samples into vapor. Examples of suitable vaporizers include a flash vaporizer, a laser ablation vaporizer, an electrospray vaporizer, and a matrix assisted laser desorption vaporizer. In other embodiments, the analyte source 36 further includes a gas chromatography column configured to pre-separate the analyte mixture before it is introduced into the injection tube 18. Such pre-separation can be useful for the case where the analyte mixture includes a solvent, such as water, nitrogen, or air, while molecules of interest in the mixture are less concentrated. In some embodiments, the analyte source 36 includes a cryo-concentration stage to increase a signal from trace constituents.

In operation, the buffer gas source 25 provides the cold buffer gas through the fill line 24 or 24'. At the same time, the analyte source 36 provides the hot analyte mixture through the injection tube 18. As a result, the gap 22 includes hot analyte molecules moving towards the aperture 16 and cold buffer gas atoms moving away from the aperture 16. Advantageously, efficient cooling of the hot analyte molecules can be achieved with a low buffer gas density, which in the vicinity of the aperture 16 can be in the range of about $10^{12}$ atoms cm$^{-3}$ to about $10^{16}$ atoms cm$^{-3}$, such as from about $10^{12}$ atoms cm$^{-3}$ to about $10^{15}$ atoms cm$^{-3}$, from about $10^{12}$ atoms cm$^{-3}$ to about $10^{14}$ atoms cm$^{-3}$, or from about $10^{13}$ atoms cm$^{-3}$ to about $10^{15}$ atoms cm$^{-3}$. As used herein, "cold" and "hot" do not necessarily imply a specific numerical value of temperature, but can be used in a relative sense to indicate that the buffer gas is colder than the analyte mixture. In some embodiments, a hot gas is at a temperature such that it has a significant vapor pressure, such as at least or greater than about $10^{-10}$ Torr.

The hot analyte molecules drift from the injection tube 18 toward the aperture 16. As they do so, they encounter the buffer gas atoms that are exiting the aperture 16. This results in thermalization as collisions, which can be elastic or inelastic, and which occur between the hot analyte molecules and the cold buffer atoms. With each such collision, a hot analyte molecule transfers energy to a cold buffer atom. These collisions thus cool the hot analyte molecules as they traverse the gap 22. Thus, by the time the analyte molecules enter the cold cell 12 for further thermalization, the analyte molecules have already been cooled significantly. This reduces a heat load experienced by the cold cell 12 and the gas within the cold cell 12. A total flow rate of the analyte mixture as introduced through the injection tube 18 can be in the range of about 0.05 sccm to about 5 sccm, such as from about 0.1 sccm to about 4 sccm, from about 0.1 sccm to about 3 sccm, from about 0.1 sccm to about 2 sccm, or no greater than or less than 2 sccm.

Once the analyte molecules enter the cold cell 12, the analyte molecules continue to thermalize with the cold buffer gas, which in turn thermalizes with the walls of the cold cell 12. In addition, the analyte molecules eventually diffuse to the cold cell walls, where the analyte molecules freeze and are effectively lost from spectroscopic analysis. Collisions with buffer gas atoms have the additional benefit of slowing the diffusion of the analyte molecules, thus increasing an average time that an analyte molecule remains in the gas phase within the cold cell 12. The flow rate and density of the buffer gas are selected to reflect a compromise between slowing diffusion of the analyte molecules in order to retain them in the cold cell 12, while mitigating against too much buffer gas such that the analyte molecules fail to enter the cold cell 12 in sufficient numbers, and while maintaining a high spectral resolution. If an average time between collisions of analyte molecules and buffer gas atoms is $\tau$, the spectral resolution of some embodiments can be proportional to $1/\tau$. Lower buffer gas densities therefore can translate into narrower spectral lines and higher spectral resolution. In some embodiments, a lifetime of the analyte molecules within the cold cell 12 is in the range of about 1 ms to about 20 ms.

The cold cell 12 is maintained at a low temperature, such as up to about 12 K, up to about 10 K, up to about 8 K, up to about 6 K, up to about 5 K, up to about 4 K, or up to about 3 K, and down to about 1 K, down to about 0.5 K, or another lower threshold that can mitigate against condensation of the buffer gas out of the gas phase. The cold cell 12 can be shaped as a cube having sides of about 8 cm to about 20 cm, although other shapes and extents are contemplated for the cold cell 12.

The apparatus 10 of FIGS. 1 to 3 provides a number of advantages for delivery of a gas phase analyte mixture into the cold cell 12. Specifically, the analyte molecules can be delivered to the cold cell 12 while mitigating against the introduction of an undesired heat load to the cold cell 12. This is accomplished by having the buffer gas cooled separately outside the cold cell 12, and by reducing the flow rate of the buffer gas. This lower buffer gas flow rate further reduces the undesired heat load.

In many cases, a final density of cold analyte molecules is set by inelastic collisions between analyte molecules. These collisions can lead to spectroscopically undetectable molecular clusters. Such collisions tend to take place at a location in the cold cell 12 with the highest analyte density. In the apparatus 10 described herein, the location with the highest density of cold analyte molecules, such as within the cold cell 12 and close to the aperture 16, has modestly higher analyte density than the analyte density in the center of the cold cell 12, thus reducing cluster formation.

Also, the widths of spectral lines in the microwave regime are typically set by collisional broadening. Lower buffer gas density and lower total gas density lead to fewer collisions, and therefore greater spectroscopic resolution for microwave spectroscopy. The apparatus 10 described herein delivers analyte molecules into the cold cell 12 at significantly lower buffer gas densities and significantly lower total gas densities than other approaches.

The ability to analyze complex, unknown chemical gas phase mixtures renders embodiments of this disclosure applicable in many areas. In particular, embodiments can be used to analyze biomedical mixtures, such as blood, urine, breath, or extracts from tissue samples; pharmacological mixtures, such as drugs and drug metabolites; environmental mixtures, such as water samples, air samples, or industrial waste samples; food mixtures, such as food products, to monitor both wanted and unwanted components; geological mixtures, such as soil and rock samples relevant to prospecting; industrial mixtures; and a priori unknown biological mixtures, such as substances produced by plants, animals, or cultured cells.

Example

The following example describes specific aspects of some embodiments of this disclosure to illustrate and provide a description for those of ordinary skill in the art. The example should not be construed as limiting this disclosure, as the example merely provides specific methodology useful in understanding and practicing some embodiments of this disclosure.

Cooling Molecules in a Cell for FTMW Spectroscopy

As set forth in this example, five different large molecules (>5 atoms) are cooled and detected to demonstrate a robust, general technique for producing continuous, high densities of large cold molecules via buffer gas cooling. Specifically, gas phase benzonitrile, acetone, 1-2 propanediol, fluorobenzene, and anisole molecules are produced in a cell at a temperature of about 8 K, and detected via FTMW spectroscopy. Helium buffer gas is used to cool the molecules originating from a high flux room temperature beam. The cooling technique offers spectral resolution that is at least comparable to seeded pulsed supersonic beam/FTMW spectroscopy but with higher number sensitivity. The helium density in this example (about $10^{14}$ He cm$^{-3}$) is significantly lower than other buffer gas sources of large cold molecules. This relatively low-collision environment allows the molecules to be detected via FTMW spectroscopy with linewidths of about 20-200 kHz, and opens the door to producing cold, slow, continuous beams of molecules for high resolution spectroscopy. The technique is also an attractive tool for quantitative studies of cold molecule-helium and molecule-molecule elastic and inelastic collisions. Data on helium molecule low temperature rotational and vibrational relaxation cross-sections are presented. Applications of the technique as a sensitive broad spectrum mixture analyzer and a high resolution slow-beam spectrometer are discussed.

Experimental

The cooling technique involves injecting warm molecules into a buffer gas cell while minimizing or reducing undesired heat loads on a buffer gas in the cell. A hot beam source is positioned outside but close to the cell, thereby substantially eliminating thermal contact between a hot injection tube and a cold vapor in the cell. This disconnect allows the injection tube to be substantially hotter and larger, as compared with an in-cell capillary.

An experimental setup was similar to that shown in FIG. 1 and FIG. 2. A hot (about 300 K, about 0.5 cm diameter) injection tube is held about 2 cm away from a circular aperture (about 1.25 cm diameter) in a cold cell (about 7-12 K, 8 cm×8 cm×8 cm), which is anchored to a cold stage of a commercial pulse tube refrigerator. Aluminized mylar superinsulation around the warm injection tube reduces the radiative heat load on the cell to about 1.5 Watts. Cold (about 7 K, about 0.2 cm diameter) fill lines deliver helium gas either to an annular manifold around the aperture or to an intake manifold on the opposite side of the cell.

A relatively large flow (typically about $2\times10^{18}$ molecules s$^{-1}$, or about 3 sccm) of warm molecules exits the tube and flies ballistically towards the cell. As the molecules travel, the molecules collide with helium atoms exiting the cell. The collisions both cool and slow the incoming molecules. Since most or almost all molecules have a mass significantly larger than that of the helium buffer gas atoms, it takes many (about 20) collisions to fully thermalize a hot molecule. According to one model, the molecules fly more or less ballistically through a counter-propagating helium cloud until the molecules are within the cell. Simulations support this model and indicate that about 10-20% of the molecules emitted from the hot tube are thermalized within the cell, the fraction being set approximately by a solid angle of the aperture as viewed from the injection tube. The flow rate of cold helium is tuned to a level high enough to provide the molecules with an in-cell diffusion time of a few ms, but low enough that the molecules are not stopped close to the aperture, where the molecules can be pushed away from the cell and lost. In this example, this helium flow rate falls in the range of about 2-8 sccm, and a molecule free induction decay signal strength is moderately sensitive to variations in the helium flow rate.

Once molecules enter the cell, the molecules continue to thermalize with the cold helium gas, which in turn thermalizes with the cell walls. At this stage, two competing processes can occur in the cell: (1) molecules diffuse to the cold cell walls, where the molecules freeze and are lost; and (2) heat diffuses to the walls, where the helium buffer gas is cooled to the cell temperature of about 7 K by absorption and desorption. Both simulations and experimental data indicate that the thermalization process is more rapid than diffusion. This is to be expected for a molecule $\chi$ such that the helium-$\chi$ total cross-section is at least modestly larger than the helium-helium elastic cross-section.

Figure 4:
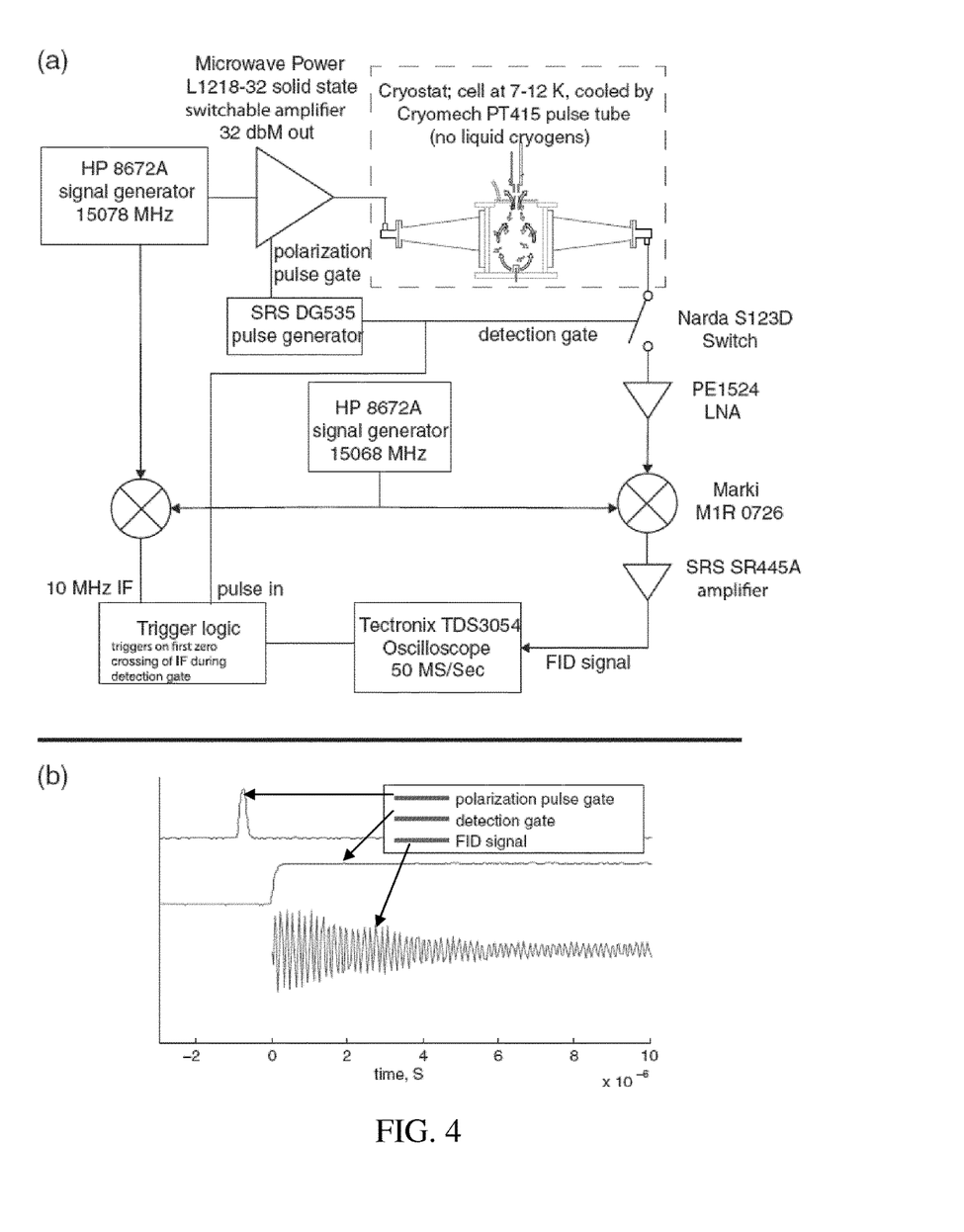

Cold molecules are detected via FTMW spectroscopy using a microwave circuit as shown in FIG. 4. Since a continuous source is used (instead of a pulsed source), a microwave pulse/detect sequence can be repeated essentially as fast as a rotational rethermalization rate. The experimental setup used can record narrow band (about 10 MHz) spectra of pure chemicals with a signal-to-noise ratio>about 500 in about 30 s of integration time. Further refinements, such as using a dedicated 350 MHz bandwidth signal averager with reduced dead time (e.g., Agilent U1084A) can reduce experimental runtimes by a factor of more than about 100.

Although the microwave circuit of this example is configured to excite and digitize a narrow (about 10 MHz) portion of the spectrum at a time, the technique can be extended to broadband applications. In particular, there should be little or no degradation of signal and a significant gain in bandwidth in moving to a chirped-pulse FTMW setup configured to digitize large portions of a microwave spectrum in a single pulse.

Figure 5:
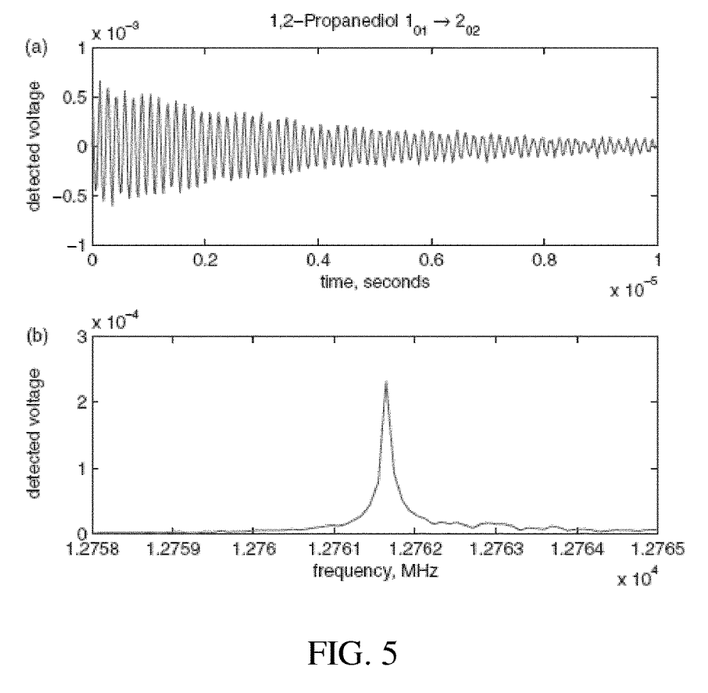
FIG. 5: Free induction decay signal of 1,2 propanediol, lowest energy conformer, $1_{01} \rightarrow 2_{02}$ at about 7.5 K. (a) The time domain signal: This signal represents 15,000 averages, or about 30 s of real time data acquisition (about 200 ms of actual integration). (b) The Fourier transform, showing the expected peak at about 12,761.6 MHz.

Results:

The experimental setup was used to cool and detect five different molecules: benzonitrile, acetone, 1-2 propanediol, fluorobenzene, and anisole. FIG. 5 shows a typical trace of a free induction decay (FID) signal from cold (about 8 K) 1-2 propanediol on the $1_{01} \rightarrow 2_{02}$ transition of the ground state conformer. This trace represents 15,000 averages, or about 30 s of experiment time. Estimates for conditions during this pulse are 1-2 propanediol total density n of about $2\times10^{12}$ cm$^{-3}$, helium density $n_{He}$ of about $2\times10^{14}$ cm$^{-3}$, temperature T of about 7.5 K, and total radiated microwave power of about 6 picoWatts (−82 dBm).

Figure 6:
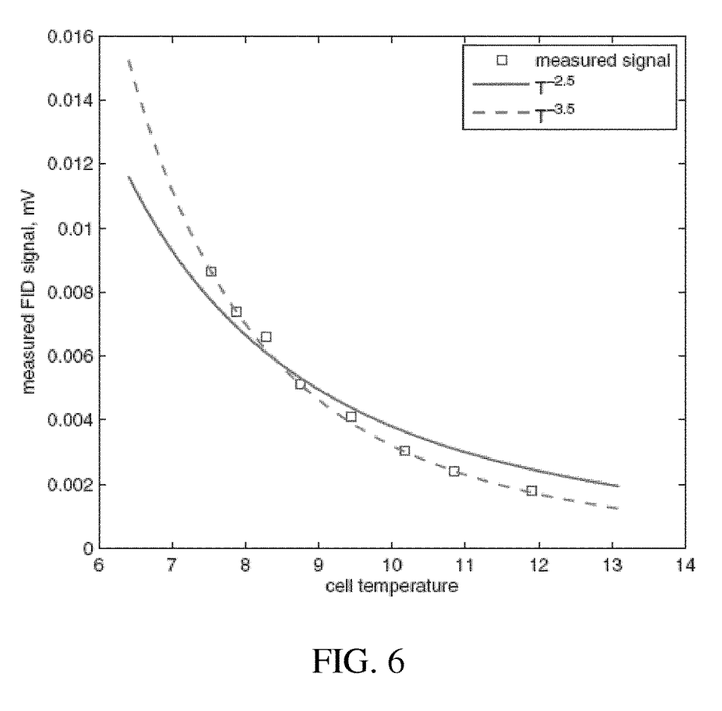
FIG. 6: Measured acetone free induction decay signal as a function of cell temperature, as measured by a diode thermometer on the outside of a cell. At a substantially constant molecule density, a measured voltage is expected to vary as $T^{5/2}$. A faster observed variation indicates that the total density of molecules also rises as the temperature drops.

FIG. 6 shows the amplitude of the $0_{00} \rightarrow 1_{11}$ transition in acetone at about 15,074.1 MHz as a function of cell temperature. The predicted scaling as $T^{-5/2}$ is shown for comparison. The measured signal seems to grow as $T^{-7/2}$, regardless of which molecule or rotational transition was observed. An explanation for this difference is that the diffusion time and hence the molecule density in the cell also vary as $T^1$. At lower temperatures, the molecules diffuse more slowly as a result of a slower molecular thermal velocity. In addition, the helium density in the cell increases if the helium flow rate is held constant and the temperature is lowered, further increasing molecular diffusion times. The observed dependence on temperature provides evidence that the molecules are close to equilibrium with the cold cell walls.

FIG. 6 indicates that further benefits can be attained from a lower cell temperature. Lower cell temperatures can be attained by, for example, controlling undesired heat loads, thereby extending temperatures down to about 3K or down to about 1K.

Inelastic Scattering

Figure 7:
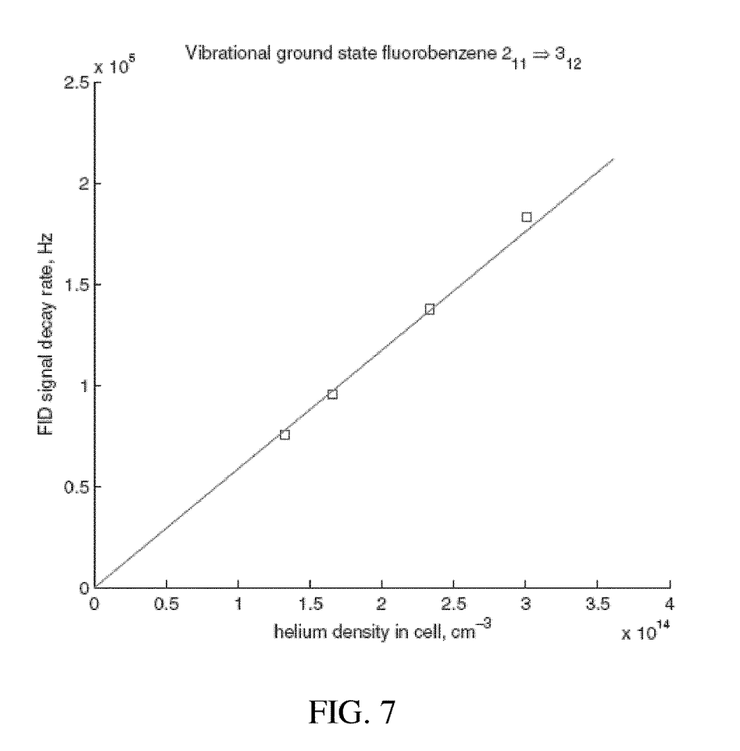
FIG. 7: Measured decay rate (squares) of a free induction decay signal of fluorobenzene as a function of helium density. The linear scaling with helium density is expected in the case where collisional broadening is dominant. The line shows the expected decay rate for $\sigma_{inelastic}$ of about $2.9 \times 10^{-14}$ cm$^2$.

Rotational inelastic cross-sections were measured for collisions between helium and acetone, fluorobenzene, and several conformers of 1-2 propanediol. FIG. 7 shows the decay rate of the FID signal of the $2_{11} \rightarrow 3_{12}$ transition of fluorobenzene as a function of helium gas density. The signal decay rate scales approximately linearly with helium density, as would be expected if collisional broadening was dominant. The combination of the measured decay rate and the known helium density and temperature yield an inelastic rotational relaxation cross-section, in this case $\sigma_{inelastic}$ of about $2.9 \times 10^{-14}$ cm$^2$.

The FID signal is expected to decay according to:

$$S(t) \propto \exp(-t/T_1)\exp[-t/T_2)] \cos(\omega_0 t),$$

where $T_1$ describes the rate of thermal relaxation of level populations, and $T_2$ describes dephasing, in this case from collisions with background helium atoms that change the phase of the molecule but not the state. In a semi-classical representation, $T_1$ describes the rate of collisions which change the angular momentum of the molecule, and $T_2$ describes the rate of collisions which leave the angular momentum unchanged, but reorient the molecular axis. A typical rethermalization collision takes the molecule from one of the two states involved in the FID to one of a potentially large number of nearby states. As the molecule gets larger, this representation would indicate that $T_1$ will decrease while $T_2$ will remain substantially unchanged, as more and more nearby rotational states become available.

On the Bloch sphere, these two processes can be seen as returning the polarization vector to the south pole (thermal relaxation, $T_1$), or distributing the vector around the equator of the sphere (decoherence, $T_2$). If dephasing were the dominant process, a rapid repeat of an experiment after time t, where $T_1 > t > T_2$, would result in a substantially smaller signal, as a π/2 pulse applied to molecules distributed at random on the equator of the Bloch sphere typically would not result in a macroscopic polarization. No such decrease is observed, and it is therefore expected that $T_1 \leq T_2$, as seen in room temperature experiments and in agreement with the semi-classical representation.

Table 1 shows the measured 8 K helium-χ inelastic rotational cross-section for various transitions in various species. The cross-sections vary modestly with molecule, conformal state, and rotational state. Such variations are expected to increase with decreasing temperature, as fewer energetically allowed channels and fewer partial waves are involved in the collision. Values of rotational relaxation cross-sections for large molecules (>5 atoms) in Table 1 are a factor of about 5-10 larger than low temperature rotational relaxation cross-sections of H$_2$CO and CH$_3$F measured via collisional broadening in mm-wave absorption spectroscopy.

TABLE 1

Molecule-helium inelastic cross-sections for a representative sample of molecules and states. The measured cross-sections are all significantly larger than the He-He elastic cross-section at this temperature of about $5 \times 10^{-15}$ cm$^2$.

| Species | Transition | σ (cm$^2$) |
|---|---|---|
| 1-2 Propanediol Conformer 2 | $1_{01} \Rightarrow 2_{02}$ | $5.2 \times 10^{-14}$ |
| 1-2 Propanediol Conformer 3 | $1_{01} \Rightarrow 2_{02}$ | $4.6 \times 10^{-14}$ |
| 1-2 Propanediol Conformer 3 | $3_{12} \Rightarrow 4_{04}$ | $3.8 \times 10^{-14}$ |
| Fluorobenzine | $2_{11} \Rightarrow 3_{12}$ | $2.8 \times 10^{-14}$ |
| Acetone | Torsional state Q, $0_{00} \Rightarrow 1_{11}$ | $2.6 \times 10^{-14}$ |

Molecule Density

Under the assumption that the dominant loss mechanism in the cell is diffusion to the cold walls, and that the molecule-helium elastic collision rate is comparable to the measured molecule-helium inelastic collision rate of about 100 kHz, the diffusion time of a molecule to the cell walls is calculated to be about 5 ms. This diffusion time, combined with a calculated input flux of about $2 \times 10^{17}$ molecules s$^{-1}$ indicates a total molecule number N of about $1 \times 10^{15}$, and a mean density n$_{molecule}$ of about $2 \times 10^{12}$ molecules cm$^{-3}$, Vibrational Modes and Conformers Inelastic molecule-helium vibrational relaxation cross-sections are typically significantly smaller than rotational relaxation cross-sections. In supersonic jets, molecules typically experience thousands of "warm" collisions at intermediate temperatures, and very few collisions at low temperatures. In this example, the situation is essentially the reverse: molecules in the buffer gas source experience hundreds or thousands of cold (<10 K) collisions with helium atoms and very few (<10) collisions at higher energies (>100 K).

Figure 8:
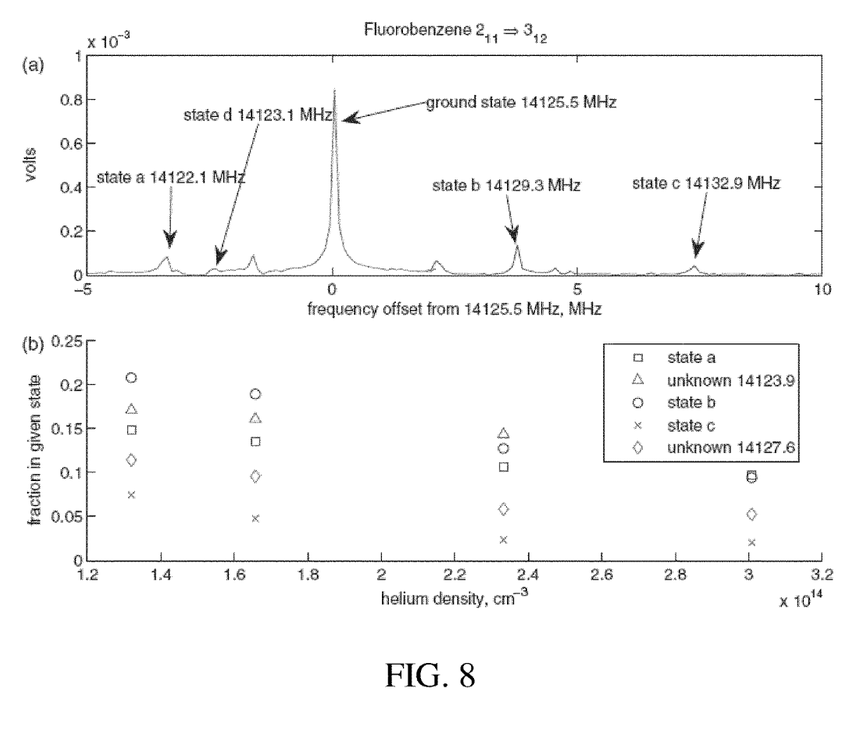
FIG. 8: (a) Fourier transform microwave spectrum in the neighborhood of the $2_{11} \rightarrow 3_{12}$ transition in fluorobenzene. The ground vibrational state and several satellite peaks can be observed. (b) The relative population of various vibrationally excited states compared to the ground state population as a function of helium density. The decreasing vibrationally excited population at high density is indicative of thermalization as the molecules undergo collisions in the cell. The spectrum shown is a combination of spectra taken separately.

FIG. 8(a) shows the spectrum of buffer gas cooled fluorobenzene in the neighborhood of its $2_{11} \rightarrow 3_{12}$ transition at about 14,125.5 MHz. Several satellite peaks, corresponding to expected vibrationally excited states of fluorobenzene, are observable. FIG. 8(b) shows the relative concentration of ground state and vibrationally excited fluorobenzene as a function of helium density; at higher densities, the fraction of excited molecules drops, as the molecules thermalize via inelastic collisions with the cold helium gas. The relaxation rate varies significantly with vibrational state. Estimates of the FBn$_a$+He→FBn$_0$ cross-section range from about $5 \times 10^{-17}$ to about $5 \times 10^{-15}$ cm$^2$, depending on the vibrational state.

Non-ground state conformers of 1-2 propanediol with energies in the 100-200 K range were also observed. Signals from torsionally excited states of acetone with similar energies of about 80 and about 125 cm$^{-1}$ were not observed, indicating that this degree of freedom thermalizes rapidly.

Applications:

Buffer Gas Cooling as a Chemical Mixture Analyzer

The high-density, continuous buffer gas source presented in this example can be advantageously used in chemical analyzers and trace gas detectors. In particular, the combination of the buffer gas source with FTMW detection can provide a general, sensitive detector that can detect trace quantities (on the order of ppb) of virtually any polar molecule. Such detector can be further enhanced with broadband chirped-pulse FTMW techniques, which take advantage of broadband synthesizers and digitizers to record large sections of the microwave spectrum simultaneously. Chirped pulse FTMW techniques, which are compatible with the high density, continuous source demonstrated in this example, can provide rapid, sensitive detection of thousands of chemical species simultaneously, and, with the incorporation of microwave-microwave or microwave-infrared double-resonance techniques, can provide excellent specificity, allowing trace compounds to be identified amid a complex chemical background.

A useful figure of merit for comparing the sensitivities of different spectroscopic devices is $F=NT^{5/2}R^{1/2}$, where N is the total number of molecules being interrogated by a given pulse sequence, T is the rotational temperature of the molecules, and R is the maximum realizable experimental repetition rate. Given similar microwave electronics, the signal-to-noise of the device and thus the lowest detectable concentration of a given component can scale linearly with F. Table 2 shows estimated N, T, R, and a scaled F, F*, for seeded free jet expansion and the buffer gas source presented in this example.

TABLE 2

Estimated total number N, rotational temperature T, physically realizable repetition rate R, and spectrometer sensitivity figure of merit F* for the source presented in this example and FTMW spectrometers based on pulsed supersonic beams. The 50 kHz R value has been realized with an updated Digital Acquisition system based on the Agilent U1084 signal averager.

| Type | N | T (K) | R (Hz) | $F^* = 1.2 \times 10^{-14}$ $NT^{-5/2}R^{1/2}$ |
|---|---|---|---|---|
| Seeded free jet expansion [40] | $10^{14}$ | 1-2 typical | 20 | 1 |
| Buffer gas source | $10^{15}$ | 5 | 50,000 | 50 |

It can be observed that the buffer gas source can have substantially more sensitivity than current state-of-the-art pulsed supersonic source spectrometers. Further improvements in sensitivity can be realized, such as through a reduction in T. It is also contemplated that the applicability of this technique as a trace gas detector or mixture analyzer can be extended to still larger molecules, such as hormones and other small biomolecules. A device with a lower cell temperature (about 5 K) and a modestly warmer (about 400 K) injection tube can be realized, allowing detection of larger, less volatile species such as the polycyclic aromatic hydrocarbon fluorine ($C_{13}H_{10}$).

Buffer Gas Source for High Resolution Spectroscopy

With the helium density tuned to maximize sensitivity, typical FID decay rates are about 100 kHz. Spectral resolution as fine as about 20 kHz has been measured in acetone spectra with the experimental setup operating at a lower helium density, and, in an optimized geometry, a resolution of less than about 10 kHz can be achievable in a buffer gas cell.

This spectroscopic resolution is significantly lower than current state-of-the-art experiments performed with coaxial seeded jet FTMW spectrometers (about 1-5 kHz typical). A higher resolution can be achieved by allowing a portion of the molecular gas/helium mixture to escape through a second aperture in the back of the cell, realizing a cold, slow, collision-free continuous beam. A proposed apparatus for such a beam is shown in FIG. 3. Such a beam can have a rotational temperature of a few K, a continuous flux $\phi$ of about $10^{15}$ molecules $s^{-1}$, a mean velocity of about 100 m $s^{-1}$, and a beam solid angle $\Omega$ of about 0.1 steradian due to the mass mismatch between the molecules and helium atoms. The low mean velocity would result in longer interaction times and ultimately higher spectral resolution, which can be set by time-of-flight broadening at about 200 Hz for a 1 m apparatus. The beam also can be a desirable source for alternating gradient Stark decelerators for large molecules.

An embodiment of this disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of an embodiment of this disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits ("ASICs"), programmable logic devices ("PLDs"), and ROM and RAM devices. Examples of computer code include machine code, such as produced by a compiler, and files containing higher-level code that are executed by a computer using an interpreter or a compiler. For example, an embodiment may be implemented using Java, C++, or other object-oriented programming language and development tools. Additional examples of computer code include encrypted code and compressed code. Moreover, an embodiment may be downloaded as a computer program product, which may be transferred from a remote computer (e.g., a server computer) to a requesting computer (e.g., a client computer or a different server computer) via a transmission channel. Another embodiment may be implemented in hardwired circuitry in place of, or in combination with, machine-executable software instructions.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, or process to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. An apparatus for spectroscopic analysis, comprising:
    a gas mixing system configured to mix a hot analyte gas that includes at least one analyte species into a cold buffer gas, thereby forming a gas mixture; and a spectroscopy module configured to characterize the gas mixture,
wherein the gas mixing system includes:
an analyte gas transport system configured to propel the hot analyte gas at a first temperature toward a volume in which the hot analyte gas is mixed with the cold buffer gas; and
a buffer gas transport system configured to propel the cold buffer gas at a second temperature toward the volume, the second temperature being lower than the first temperature.

2. The apparatus of claim 1, wherein the first temperature is at least 294 K, and the second temperature is up to 12 K.

3. The apparatus of claim 1, wherein the analyte gas transport system is configured to propel the hot analyte gas at a flow rate no greater than 2 sccm.

4. The apparatus of claim 1, wherein the buffer gas transport system is configured to propel the cold buffer gas at a flow rate in the range of 1 sccm to 10 sccm.

5. The apparatus of claim 1, further comprising a cold cell to receive the gas mixture, the cold cell including walls defining an interior chamber and a first aperture connecting the interior chamber to a first space external to the cold cell.

6. The apparatus of claim 5, wherein the analyte gas transport system includes an injection tube configured to propel the hot analyte gas across a gap and toward the first aperture.

7. The apparatus of claim 5, wherein the volume in which the hot analyte gas is mixed with the cold buffer gas includes at least a portion of the first space external to the cold cell.

8. The apparatus of claim 5, wherein the volume in which the hot analyte gas is mixed with the cold buffer gas includes at least a portion of the interior chamber of the cold cell.

9. The apparatus of claim 5, wherein a density of the cold buffer gas adjacent to the first aperture is up to $10^{16}$ atoms $cm^{-3}$.

10. The apparatus of claim 5, wherein the buffer gas transport system is configured to propel the cold buffer gas into the first space external to the cold cell.

11. The apparatus of claim 5, wherein the buffer gas transport system is configured to propel the cold buffer gas into the interior chamber of the cold cell.

12. The apparatus of claim 5, further comprising an annular manifold disposed in a periphery of the first aperture, and the buffer gas transport system is configured to propel the cold buffer gas through the annular manifold.

13. The apparatus of claim 5, wherein the spectroscopy module is configured to characterize the gas mixture within the cold cell.

14. The apparatus of claim 5, wherein the walls of the cold cell define a second aperture connecting the interior chamber to a second space external to the cold cell.

15. The apparatus of claim 14, wherein the spectroscopy module is configured to characterize the gas mixture within the second space.

16. A method for spectroscopic analysis, comprising:
mixing an analyte gas at a first temperature with a buffer gas at a second temperature lower than the first temperature, thereby forming a supersaturated gas mixture; and
directing the gas mixture to enter a cold cell,
wherein mixing the analyte gas with the buffer gas includes:
propelling the analyte gas at the first temperature toward a volume in which the analyte gas is mixed with the buffer gas; and
propelling the buffer gas at the second temperature toward the volume.

17. The method of claim 16, wherein the first temperature is at least 294 K, and the second temperature is up to 12 K.

18. The method of claim 16, wherein
a density of the buffer gas within the volume is up to $10^{16}$ atoms $cm^{-3}$.

19. The method of claim 16, further comprising characterizing the gas mixture with a spectroscopy module when the gas mixture is within the cold cell.

20. The method of claim 16, further comprising characterizing the gas mixture with a spectroscopy module when the gas mixture is in a space external to the cold cell.

* * * * *